(12) United States Patent
Martin et al.

(10) Patent No.: US 8,936,794 B2
(45) Date of Patent: Jan. 20, 2015

(54) CONDUCTING POLYMER NANOTUBE ACTUATORS FOR PRECISELY CONTROLLED RELEASE OF MEDICINE AND BIOACTIVE MOLECULES

(75) Inventors: David C. Martin, Ann Arbor, MI (US); Mohammad Reza Abidian, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 2046 days.

(21) Appl. No.: 11/895,515

(22) Filed: Aug. 24, 2007

(65) Prior Publication Data

US 2008/0097280 A1    Apr. 24, 2008

Related U.S. Application Data

(60) Provisional application No. 60/840,382, filed on Aug. 25, 2006.

(51) Int. Cl.
- *A61K 9/00* (2006.01)
- *A61K 41/00* (2006.01)
- *A61N 1/30* (2006.01)

(52) U.S. Cl.
CPC ............ *A61K 9/0092* (2013.01); *A61K 9/0009* (2013.01); *A61K 41/00* (2013.01); *A61N 1/30* (2013.01)
USPC ....................................................... 424/400

(58) Field of Classification Search
None
See application file for complete search history.

(56) References Cited

U.S. PATENT DOCUMENTS

| | | | |
|---|---|---|---|
| 1,975,504 A | 10/1934 | Formhals | |
| 4,341,221 A | 7/1982 | Testerman | |
| 4,585,652 A | 4/1986 | Miller et al. | |
| 5,031,621 A | 7/1991 | Grandjean et al. | |
| 5,092,332 A | 3/1992 | Lee et al. | |
| 5,130,412 A | 7/1992 | Wellinghoff et al. | |
| 5,368,028 A | 11/1994 | Palti | |
| 5,513,636 A | 5/1996 | Palti | |
| 6,095,148 A * | 8/2000 | Shastri et al. | 128/898 |
| 6,132,752 A | 10/2000 | Pickett et al. | |

(Continued)

FOREIGN PATENT DOCUMENTS

| | | |
|---|---|---|
| AU | 2006284625 | 3/2007 |
| AU | 2007342682 | 7/2008 |

(Continued)

OTHER PUBLICATIONS

Kim, D., et al., "Conducting polymers grown in hydrogel scaffolds coated on neural prosthetic devices", 2004, J.Biomed. Mater. Res. A, 4, pp. 577-585.*

(Continued)

*Primary Examiner* — Paul Dickinson
(74) *Attorney, Agent, or Firm* — Harness, Dickey & Pierce, P.L.C.

(57) ABSTRACT

Drug delivery devices, their manufacture, and their use comprising electrocontractile nanotubes that can be used for precise controlled bioactive substance release for example, medical, veterinary, pharmaceutical compounds and growth factors. The conducting polymer nanotubes significantly decrease the impedance and increase the charge capacity of recording electrode sites on microfabricated electrode devices. Bioactive substances released from the nanotubes can be controlled in a desired fashion by controlled electrical stimulation of the nanotubes.

22 Claims, 7 Drawing Sheets trans-polyacetylene cis-polyacetylene polyanilines polythiophene polypyrrole polydioxythiophene

(56) References Cited

U.S. PATENT DOCUMENTS

| | | | |
|---|---|---|---|
| 6,179,835 | B1 | 1/2001 | Panescu et al. |
| 6,197,881 | B1 | 3/2001 | Cosnier |
| 6,294,245 | B1 | 9/2001 | Roitman et al. |
| 6,331,244 | B1 | 12/2001 | Lewis et al. |
| 6,468,304 | B1 | 10/2002 | Dubois-Rande et al. |
| 6,482,299 | B1 | 11/2002 | Inganäs et al. |
| 6,528,020 | B1 | 3/2003 | Dai et al. |
| 6,627,154 | B1 | 9/2003 | Goodman et al. |
| 6,696,575 | B2 | 2/2004 | Schmidt et al. |
| 6,730,212 | B1 | 5/2004 | Yamagishi et al. |
| 6,753,454 | B1 | 6/2004 | Smith et al. |
| 6,890,715 | B1 | 5/2005 | Lewis et al. |
| 6,946,597 | B2 | 9/2005 | Sager et al. |
| 6,958,216 | B2 | 10/2005 | Kelley et al. |
| 7,037,319 | B2 | 5/2006 | Weber |
| 7,045,205 | B1 | 5/2006 | Sager |
| 7,070,592 | B2 | 7/2006 | Santini, Jr. et al. |
| 7,162,308 | B2 | 1/2007 | O'Brien et al. |
| 7,689,260 | B2 | 3/2010 | Finch et al. |
| 8,005,526 | B2 | 8/2011 | Martin et al. |
| 2004/0082843 | A1 | 4/2004 | Menon |
| 2004/0111141 | A1 | 6/2004 | Brabec et al. |
| 2005/0033132 | A1 | 2/2005 | Shults et al. |
| 2005/0048651 | A1 | 3/2005 | Ryttsen et al. |
| 2005/0234513 | A1 | 10/2005 | Alexander et al. |
| 2005/0263394 | A1 | 12/2005 | Lewis et al. |
| 2006/0160100 | A1 | 7/2006 | Gao et al. |
| 2007/0060815 | A1 | 3/2007 | Martin et al. |
| 2011/0087315 | A1 | 4/2011 | Richardson-Burns et al. |
| 2011/0257504 | A1 | 10/2011 | Hendricks et al. |

FOREIGN PATENT DOCUMENTS

| | | |
|---|---|---|
| CA | 2621174 | 3/2007 |
| CA | 2694431 | 7/2008 |
| EP | 1931248 | 6/2008 |
| EP | 2056878 | 5/2009 |
| JP | 4-501670 | 3/1992 |
| JP | 7-24053 | 1/1995 |
| JP | 2001-515343 | 9/2001 |
| JP | 2004-524891 | 8/2004 |
| JP | 2004-528079 | 9/2004 |
| JP | 2009-506836 | 2/2009 |
| JP | 2010-501260 | 1/2010 |
| WO | WO 90/01969 | 3/1990 |
| WO | WO 97/16545 | 5/1997 |
| WO | WO 02/060350 | 8/2002 |
| WO | WO 02/077336 | 10/2002 |
| WO | WO 2007/028003 | 3/2007 |
| WO | WO 2008/085199 | 7/2008 |
| WO | WO 2011/127166 | 10/2011 |

OTHER PUBLICATIONS

Yang, J., et al., "Microporous conducting polymers on neural microelectrode arrays I Electrochemical deposition", 2004, Sensors and Actuators B, 101, pp. 204-211.*

Abidian, M. R., et al., "Conducting-Polymer nanotubes for controlled release", 2006, Advanced Materials, 18, pp. 405-409.*

Kim, et al., "Synthesis, characteristics, and field emission of doped and de-doped polypyrrole, polyanaline, poly(3,4-ethylenedioxythiophene) nanotubes and nanowires", 2005, Synthetic Metals, 150, pp. 279-284.*

Chew, S.Y., et al., "Sustained Release of Proteins from Electrospun Biodegradable Fibers", 2005, Biomacromolecules, 6, pp. 2017-2024.*

"Sub-micrometer Conducting Polyanaline Tubes prepared from polymer fiber templates", 2004, Chem. Mater., 16, pp. 371-373.*

DiPaolo, B.C., et al., "Nanofiber scaffolding for improved neural electrode biocompatability", 2003, IEEE 29$^{th}$ conference, pp. 21-22.*

Zhang, Y., et al., "Recent development of polymer nanofibers for biomedical and biotechnoligical applications", 2005, Jourtnal of Materials Science, 16, pp. 933-946.*

Chun, Iksoo et al., "Carbon nanofibers from polyacrylonitrile and mesophase pitch," Journal of Advanced Materials, vol. 31, No. 1, pp. 36-41 (1999) (abstract only).

Hatano, Tsukasa et al., Chemistry—A European Journal, vol. 10, pp. 5067-5075 (2004) (published online Sep. 2, 2004).

Abidian, Mohammad Reza, "Functional Conducting Polymer Nanomaterials and Bioactive Polymer Nanofibers for Neural Prosthetic-Nervous System Interfaces," Doctor of Philosophy (Biomedical Engineering) Dissertation, University of Michigan, Ann Arbor: ProQuest/UMI, Publication No. 3253205 (2007).

Campbell, T.E. et al., "Incorporation of Erythrocytes into Polypyrrole to Form the Basis of a Biosensor to Screen for Rhesus (D) Blood Groups and Rhesus (D) Antibodies," Electroanalysis, vol. 11, No. 4, pp. 215-222 (1999).

Cui, Xinyan et al., "Electrochemical deposition and characterization of poly(3,4-ethylenedioxythiophene) on neural microelectrode arrays," Sensors and Actuators B: Chemical, vol. 89, pp. 92-102 (2003).

Cui, Xinyan et al., "In vivo studies of polypyrrole/peptide coated neural probes," Biomaterials, vol. 24, pp. 777-787 (2003).

Cui, Xinyan et al., "Surface modification of neural recording electrodes with conducting polymer/biomolecule blends," J. Biomed. Mater. Res., vol. 56, pp. 261-272 (2001).

Dai, Tingyang et al., "Conducting hydrogels with enhanced mechanical strength," Polymer, vol. 50, pp. 5236-5241 (2009) (published online Sep. 12, 2009).

Ghosh, Soumyadeb et al., "Electrochemical Characterization of Poly(3,4-ethylene dioxythiophene) Based Conducting Hydrogel Networks," Journal of the Electrochemical Society, vol. 147, No. 5, pp. 1872-1877 (2000).

Gilmore, K. et al., "Preparation of Hydrogel/Conducting Polymer Composites," Polymer Gels and Networks, vol. 2, pp. 135-143 (1994).

Gooding, J. Justin et al., "Electrochemical modulation of antigen-antibody binding," Biosensors and Bioelectronics, vol. 20, pp. 260-268 (2004) (published online Feb. 28, 2004).

Ito, Yuichiro et al., "Development of Electrodes with Conductive Polymer for Stimulating Nervous System," Technical Report of IEICE, The Institute of Electronics, Information and Communication Engineers, vol. 100, No. 479, pp. 33-38 (Dec. 1, 2000) (English Abstract only).

Khor, Eugene et al., "In situ polymerization of pyrrole in animal tissue in the formation of hybrid biomaterials," Biomaterials, vol. 16, No. 8, pp. 657-661 (1995).

Kim, B.C. et al., "Electroformation of conducting polymers in a hydrogel support matrix," Polymer, vol. 41, pp. 1783-1790 (2000).

Kim, Kwangsok et al., "Incorporation and controlled release of a hydrophilic antibiotic using poly(lactide-co-glycolide)-based electrospun nanofibrous scaffolds," Journal of Controlled Release, vol. 98, pp. 47-56 (2004).

Kipke, Daryl R. et al., "Silicon-Substrate Intracortical Microelectrode Arrays for Long-Term Recording of Neuronal Spike Activity in Cerebral Cortex," IEEE Transactions on Neural Systems and Rehabilitation Engineering, vol. 11, No. 2, pp. 151-155 (Jun. 2003).

Kositsky, Michael et al., "Dynamical Dimension of a Hybrid Neurorobotic System," IEEE Transactions on Neural Systems and Rehabilitation Engineering, vol. 11, No. 2, p. 155 (Jun. 2003).

Nyberg, Tobias et al., "Polymer Hydrogel Microelectrodes for Neural Communication," Biomedical Microdevices, vol. 4, No. 1, pp. 43-52 (2002).

Rahman, Md. Aminur et al., "The biosensor based on the pyruvate oxidase modified conducting polymer for phosphate ions determinations," Biosensors & Bioelectronics, vol. 21, No. 7, pp. 1116-1124 (Jan. 15, 2006) (published online May 11, 2005) (Article in Press version and publication information provided).

Reneker, Darrell H. et al., "Nanometre diameter fibres of polymer, produced by electrospinning," Nanotechnology, vol. 7, pp. 216-223 (1996).

Schmidt, Christine E. et al., "Stimulation of neurite outgrowth using an electrically conducting polymer," Applied Biological Sciences, vol. 94, pp. 8948-8953 (Aug. 1997).

(56) References Cited

OTHER PUBLICATIONS

Woerly, Stéphane, "Restorative surgery of the central nervous system by means of tissue engineering using NeuroGel implants," Neurosurg. Rev., vol. 23, pp. 59-77 (2000).

Xiao, Yinghong et al., "Electrochemical polymerization of poly(hydroxymethylated-3,4-ethylenedioxythiophene) (PEDOT-MeOH) on multichannel neural probes," Sensors and Actuators B: Chemical, vol. 99, pp. 437-443 (2004).

Yang, Junyan et al., "Microporous conducting polymers on neural microelectrode arrays II. Physical characterization," Sensors and Actuators A: Physical, vol. 113, pp. 204-211 (2004) (published online Apr. 1, 2004).

Yang, Junyan et al., "Microporous conducting polymers on neural microelectrode arrays I Electrochemical deposition," Sensors and Actuators B: Chemical, vol. 101, pp. 133-142 (2004) (published online Apr. 22, 2004).

Yang, Junyan et al., "Ordered surfactant-templated poly(3,4-ethylenedioxythiophene) (PEDOT) conducting polymer on microfabricated neural probes," Acta Biomaterialia, vol. 1, pp. 125-136 (2005).

The International Search Report and Written Opinion of the International Searching Authority issued on Sep. 11, 2008 for related PCT International Application No. PCT/US2007/018736 (published as WO 2008/085199).

The International Preliminary Report on Patentability issued on Mar. 3, 2009 for related PCT International Application No. PCT/US2007/018736 (published as WO 2008/085199).

Communication issued by the European Patent Office on Dec. 28, 2010 enclosing the Extended European Search Report and European Search Opinion dated Dec. 16, 2010 for related European Application No. 07872172.7 (published as EP 2056878 A0).

Communication issued by the European Patent Office on Jan. 14, 2011 for related European Application No. 07872172.7 (published as EP 2056878 A0).

International Search Report and Written Opinion of the International Searching Authority issued on Aug. 6, 2007 for cross-referenced PCT International Application No. PCT/US2006/034199 (published as WO 2007/028003).

International Preliminary Report on Patentability issued on Mar. 4, 2008 for cross-referenced PCT International Application No. PCT/US2006/034199 (published as WO 2007/028003).

International Search Report and Written Opinion of the International Searching Authority issued on Dec. 27, 2011 for cross-referenced PCT International Application No. PCT/US2011/031413 (published as WO 2011/127166).

Examiner's First Report issued on Jul. 12, 2011 for Australian Application No. 2006284625 (published as AU 2006284625).

Communication issued on Mar. 9, 2010 enclosing the Supplementary European Search Report and European Search Opinion dated Feb. 25, 2010 for European Application No. 06824877.2 (published as EP 1931248 A0).

Office Action issued on Mar. 26, 2010 for European Application No. 06824877.2 (published as EP 1931248 A0).

Applicant's Response to Office Action issued on Mar. 26, 2010 for European Application No. 06824877.2 (published as EP 1931248 A0) as filed on Oct. 26, 2010.

English translation of Official Action issued on Nov. 22, 2011 for Japanese Application No. 2008-529303 (published as JP 2009-506836), translation provided by Asamura Patent Office, P.C.

\* cited by examiner trans-polyacetylene cis-polyacetylene polyanilines polythiophene polypyrrole polydioxythiophene

CONDUCTING POLYMER NANOTUBE ACTUATORS FOR PRECISELY CONTROLLED RELEASE OF MEDICINE AND BIOACTIVE MOLECULES

CROSS-REFERENCE TO RELATED APPLICATIONS

This application claims the benefit of U.S. Provisional Application No. 60/840,382, filed on Aug. 25, 2006, the disclosure of which is hereby incorporated by reference.

GOVERNMENT RIGHTS

This invention was made with government support under NS012338 from the National Institutes of Health. The government has certain rights in the invention.

FIELD

The present disclosure relates to biocompatible, biologically interfaced implantable devices capable of controlled bioactive substance delivery. The enhanced bioactive substance release is intimately coupled with probes and stimulation/sensing devices having effective three-dimensional integration into living tissue and other biological matrices for applications relating to neural prostheses, biosensors, targeted nanodelivery, and nanofiltration.

BACKGROUND

There are several surgical and non-surgical modalities that require the precise delivery of medicines and drugs to the site of disease. Often, these sites may also require an implanted device or prosthesis in addition to deliver such drugs, to perform one or more sensory or stimulatory functions, such as in a heart electrophysiological assessment or neural scanning.

Inherently "conducting polymers" (π-conjugated conductive polymers) for example, poly(3,4-ethylenedioxythiophene) (PEDOT), poly(pyrrole), polyanilines, polyacetylenes, polythiophenes, polymer blends thereof and non-conducting polymers with conducting dopants are useful as biocompatible polymeric coating materials for preexisting electrodes, probes and sensors, providing unique electrical, biochemical and electroactive properties. The inherently conducting monomers can comprise one or more of (3,4-ethylenedioxythiophene) (EDOT), pyrrole, anilines, acetylenes, thiophenes, and monomer blends thereof.

Several developments in the field of electrochemical delivery of bioactive agents have yielded electrode devices that incorporate a conducting polymer that is electrochemically cycled between a charged or neutral state. The premise behind this mode of operation includes employing a conducting polymer electrode wherein the conducting polymer is for example, charged cathodically or anodically while in contact with an aqueous medium. The drug to be delivered must exist in the form of a counterion causing the drug to bind ionically. Such devices are described in U.S. Pat. No. 4,585,652.

The use of such drug delivery is disadvantageous, since the selection of drug or pharmaceutical must comply with it's counterion function and limits the selection of bioactive substances to be delivered. Furthermore, the bioactive agent cannot comprise both anions and cations in a single delivery cycle and cannot deliver bioactives that do not have a specific charge or are neutral. Further limitations which are placed on the use of bioactive agents coupled to conducting polymers include limits on the amount of coupled bioactive agent to be delivered. Invariably, the upper limit of material that can be delivered in such delivery devices is around 50% of the polymer used, since there is a finite amount of charged conducting polymer to bind the chemical in its redox sites. (Typically one charge per three molecules of monomer).

It would be highly desirable to design electrode devices which could intimately interface electrode sites to living tissue, and thus create charge transport from ionically conducting tissue to the electronically conducting electrode and induce surrounding tissue to attach or interface directly to the implanted device and are capable of delivering any species of bioactive substance notwithstanding charge and quantity limitations.

SUMMARY

The present disclosure provides drug delivery devices, electrodes and sensors comprising one or more electrically conductive substrate in contact with a plurality of electrocontractile nanotubes. The nanotubes are coated on at least a portion of a conductive substrate. The nanotube comprises at least one opening and walls of conductive polymer defining a lumen therein. The lumen contains at least one bioactive substance. A power source can be connected to the conductive substrate(s) and provide a voltage to electrically actuate at least a portion of the nanotubes, causing the release of the bioactive substance from the nanotube through one or more openings by mass transport.

A further aspect of the present disclosure provides a method of forming nanotubes on an electrically conductive substrate. The nanotubes are formed on at least a portion of a first electrically conductive substrate comprising the steps: (i) electrospinning a solution comprising a biodegradable polymer and at least one bioactive substance onto at least a portion of a surface of the first electrically conductive substrate, The electrospinning procedure thereby forms a mesh of nanofibers in contact with the first electrically conductive substrate; (ii) electrochemically depositing conductive polymers around the nanofibers forming a plurality of nanotubes; and (iii) degrading the biodegradable polymer within the nanofibers with a solvent, thereby leaving bioactive substance inside the lumen of the nanotubes.

A further aspect of the present teachings further includes one or more bioactive substance, wherein the bioactive substance can be one or more of drug, pharmaceutical active, growth factor, lipid, steroid, carbohydrate, carbohydrate derivative glycoprotein, glycolipid, antisense agent, antineoplastic agent, antiproliferative agent, antithrombogenic agent, anticoagulant, antiplatelet agent, antibiotic, anti-inflammatory agent, gene therapy agent, therapeutic substance, organic drug, pharmaceutical compound, recombinant DNA product, recombinant RNA product, collagen, collagenic derivative, protein, protein analog, or combinations thereof.

A further aspect of the present teachings relates to a method for controlled release of one or more bioactive substances. The method includes providing a drug delivery device comprising at least two electrically conductive substrates, a plurality of electrocontractile nanotubes formed on at least a portion of one of the conductive substrates. The nanotubes comprise walls of conductive polymer defining a lumen therein, wherein the lumen contains at least one bioactive substance. The method further includes providing a power source in electrical communication with at least one of the electrically conductive substrates. The device is then placed in contact or in proximate location with a biological tissue, for example in the brain or heart and applying a voltage to at least one of the electrically conductive substrates of the device so as to supply a voltage to the conductive polymer walls of the nanotubes, thereby causing a contraction of said nanotubes and concomitant release of said at least one bioactive substance.

Further areas of applicability of the present teachings will become apparent from the detailed description provided hereinafter. It should be understood that the detailed description and specific examples, while indicating certain embodiments of the invention, are intended for purposes of illustration only and are not intended to limit the scope of the invention.

DRAWINGS

The drawings described herein are for illustration purposes only and are not intended to limit the scope of the present disclosure in any way.

Figure 6:
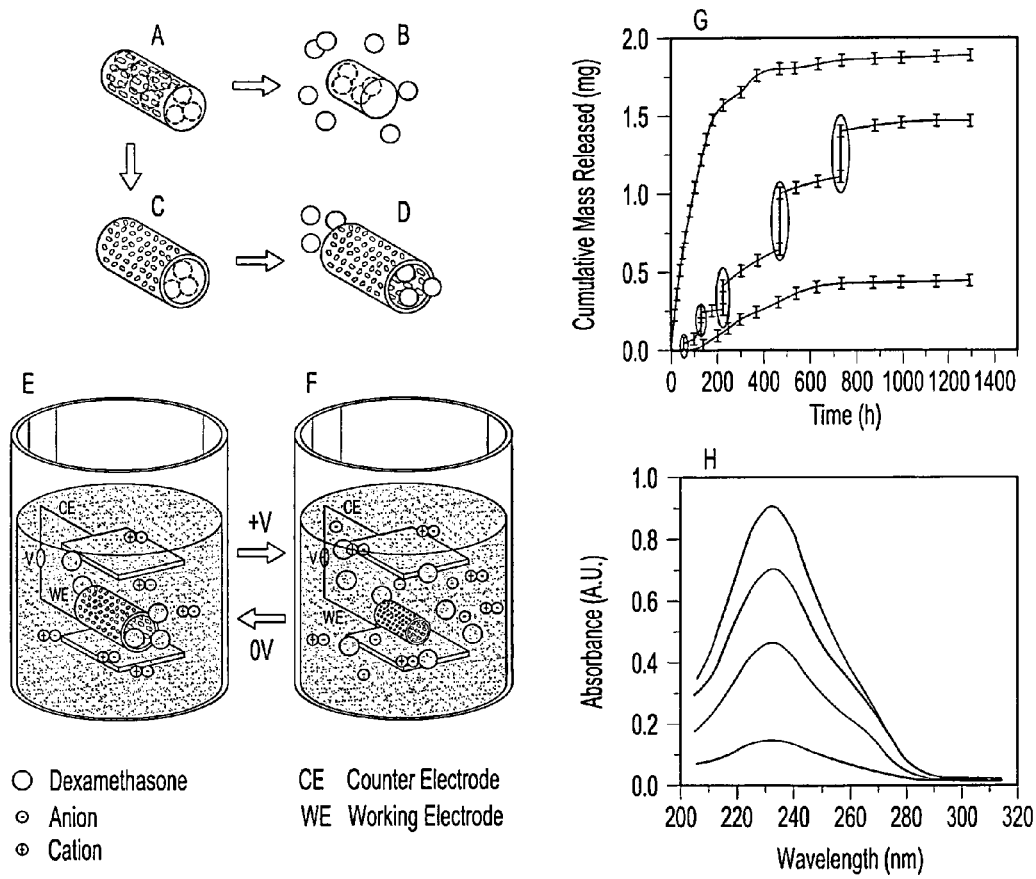
Figure 7:
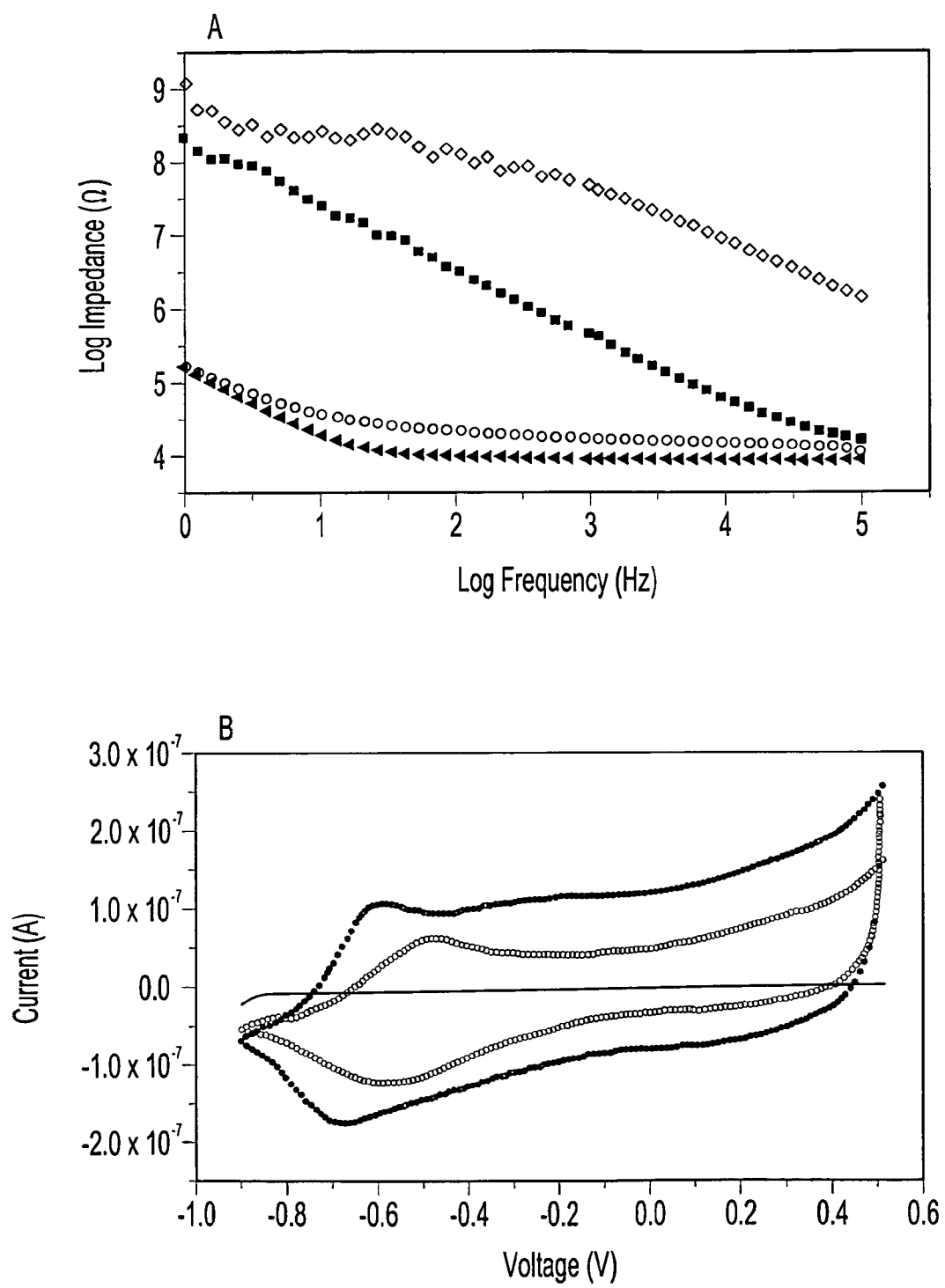

FIG. 6 shows illustration of the controlled release of Dexamethasone (Illustrations FIGS. 6A-6F), FIG. 6G depicts release rates of Dexamethasone in PGLA nanofibers, PLGA nanofibers containing Dexamethasone coated with conducting polymer and stimulated with 5 electrical stimulations and PLGA nanofibers containing Dexamethasone coated with conducting polymer without electrical stimulations in accordance with the present disclosure, FIG. 6H depicts the UV absorbance of Dexamethasone FIG. 7A depicts the impedance spectroscopy of electric conducting nanotubes on gold electrodes versus bare gold electrodes in accordance with the present disclosure.

FIG. 7B depicts cyclic voltammogram recorded for electrodes with no nanotubes, with PLGA nanofibers and electrochemical deposited PEDOT, or PEDOT nanotubes with the PLGA core fiber material removed in accordance with the present disclosure.

DETAILED DESCRIPTION

The present disclosure exemplifies in some embodiments, the interactions of neural cell types and brain tissue with the conducting polymers poly(3,4-ethylenedioxythiophene) (PEDOT), poly(pyrrole) and other conducting polymers for tissue stimulation, recording and nanoscale to microscale delivery of bioactive substances. In various embodiments, the present disclosure includes electrochemical polymerization of PEDOT, PPy and other electrically conducting polymers and their derivatives around nanoscale fibers and particles loaded with bioactive substances including: growth factors, drugs, pharmaceuticals and other bioactive agents.

The biocompatible conducting polymers contemplated by certain embodiments of this disclosure include, but are not limited to: biocompatible conducting polymer coatings which have low biodegradability, or are substantially non-biodegradable, low electrical impedance, long-term electrical stability under in vivo conditions, is non-toxic, is mechanically soft, is highly biomimetic (can be cell feature/cell surface templated & patterned) with nanometer scale surface features. The present disclosure further includes conducting polymer nanotubes and nanoparticles that can be electrically stable over time following implantation in tissue, relatively non-biodegradable yet highly biocompatible, eliciting lower levels of immunoreactivity than commonly used electrode and microfluidic materials such as silicon, platinum, iridium, indium tin oxide, and tungsten rubber, and plastic. In certain embodiments, the conducting polymer nanotubes or nanoparticles can be loaded to maintain and release in a highly controlled manner, a variety of bioactive substances including, but not limited to pharmaceutical agents and growth factors to facilitate interactions with specific proteins or biomolecules and living cells. These bioactive substances can be incorporated into biodegradable nanofibers via any commonly known nanoscale fabrication method including electrospinning methods. The nanotubes are then formed by electrochemical deposition of conducting polymers around the electrospun nanoscale fibers. These enhanced biocompatible conducting polymer nanotubes and nanoparticles can be exploited to make the conducting polymer nanotubes or nanoparticles bioactive as well as to make possible reversible changes in electrical conductivity triggered by specific stimuli thus allowing the polymer film to act as a biomolecule sensing device. In some embodiments, the devices described in the present teachings can function as stimulating and/or sensing devices before or after the bioactive substances have been delivered. In some embodiments, the conducting polymer nanotubes and nanoparticles can be soft, fuzzy materials with low electrical impedance and enormous surface areas. The large surface area can be ideal for facilitating maximal charge transfer between the electrode and target tissue wherein the pliability of the polymer can allow for decreased mechanical strain at the interface between the soft tissue and the hard device surface compared to a metal electrode. The disclosed conducting polymer electrodes can serve as novel high surface area, soft, biocompatible, and electrically stable surface coatings for existing electrode-based biomedical devices that will result in decreased immunoreactivity and improved signal transduction at the interface between the tissue and the device.

The use of conducting polymers patterned on the surface of electrode substrates facilitates signal transport from ionically conducting tissue to the electronically conducting electrode array. In certain embodiments, the present disclosure provides for novel conducting polymer networks having the capability of targeted nanodelivery and nanofiltration as well as a process for polymerizing conducting polymers around degradable nanofibers and nanoparticles optionally in the presence of living cells and other biological scaffolds, including hydrogel and complex polysaacharide and protein based scaffolds including collagen, alginate, gelatin, resulting in devices having intimate and direct interfacing capabilities between the surface of an electrode-based substrate and a biological entity. As defined herein, a biological entity is any biological organ, tissue, cell, cell component or constituent including for example enzymes and other cellular constituents.

A. Electrode Compositions

Electrode Substrates

Electrode substrates can comprise any conducting material and groups of conducting materials. A number of exemplary electrode substrate configurations are described and can be understood that other configurations can be used. In non-limiting embodiments, electrode substrates can be manufactured from metals including, but not limited to: Gold (Au), Platinum (Pt), Iridium (Ir), Palladium (Pd), Tungsten (W), Stainless Steel (SS), Indium-Tin-Oxide (ITO), Zinc, Titanium (Ti) and their alloys and oxides. Other conducting electrode substrates useful in the present disclosure include: carbon, carbon composites, conducting ceramics, for example, doped silicon (Si) and conducting polymers that are capable of conducting electrons including polyanilines, polypyrroles, polythiophenes, polydioxythiophenes and combinations of these.

In certain embodiments, the conducting substrate can be interfaced with electrical biasing or stimulating devices and electrical detection or sensing devices. In some embodiments the electrode substrate can be biased with galvanostatic current which can be applied to the electrode using an AutoLab Potentiostat/Galvanostat (EcoChemie, The Netherlands) or some similar instrument capable of delivering direct current (DC) at 0.1-100 $\mu A/mm^2$ for a period of time, ranging from 0 to 360 minutes depending on the desired thickness of the polymer film. Electrochemical oxidation/reduction of the monomer around the electrode substrate can result in the formation of conducting polymer films and networks coated around the nanofibers preloaded with bioactive substances and optionally in the presence of live cells, thus embedding the nanofibers coated with conducting polymer and optionally cells and immobilizing them in a conducting polymer scaffold.

Biocompatible Nanofibers

In various embodiments, the electrode substrate is in contact with a biocompatible and biodegradable scaffold network of nanofibers. Nanofibers can be produced in a variety of methods. In some embodiments the nanofibers can be produced using any commonly known method of nanofiber production used in the military garment, nanofiltration and tissue engineering arts, including, but not limited to electrospinning, meltspinning and fiber extrusion techniques. Common electrospinning techniques can be found in: Formhals, A., Process and Apparatus for Preparing Artificial Threads", U.S. Pat. No. 1,975,504, Oct. 2, 1934., Chun, I., U.S. Pat. No. 6,753,454 Smith, et al 2004, Reneker, D. H., Fong, H., Fang, X., Deitzel, J., Beck Tan, N., Kearns, K., "Carbon Nanofibers from Polyacrylonitrile and Mesophase Pitch", Journal of Advanced Materials, Volume 31, Number 1, January 1999, pages 36-41, and Reneker, D. H., and Chun, I., "Nanometer Diameter Fibres of Polymer, Produced by Electrospinning", Nanotechnology, Volume 7, 1996, pages 216-233.

In various embodiments, the polymers used to make the nanofibers or nanoparticles can include one or more of: degradable polymers such as: poly(d, lactic acid) (PDLA), poly(l, lactic acid) (PLLA), poly(lactide-co-glycolide) (PLGA) poly (glycolic acid) (PGA), and their derivatives, poly (epsilon caprolactone) (PCL), chitosan, Nylon, PEOxide, alginates, poly vinyl alcohol and combinations thereof. In certain embodiments, the nanofiber polymer solution contains degradable polymer which can be electrospun directly onto the electrode substrate. The polymer can at this point prior to deposition near or on the electrode substrate surface be admixed with the one or more bioactive substances. In various embodiments, the concentration of degradable polymer to bioactive substance can range from 1:99 to 99:1 v/v. The concentration ratio between polymer and bioactive substance can depend on several factors including intended application, quantity of nanofiber produced, duration of nanoscale delivery of the bioactive substance, and concentration of the bioactive substance.

Figure 3:
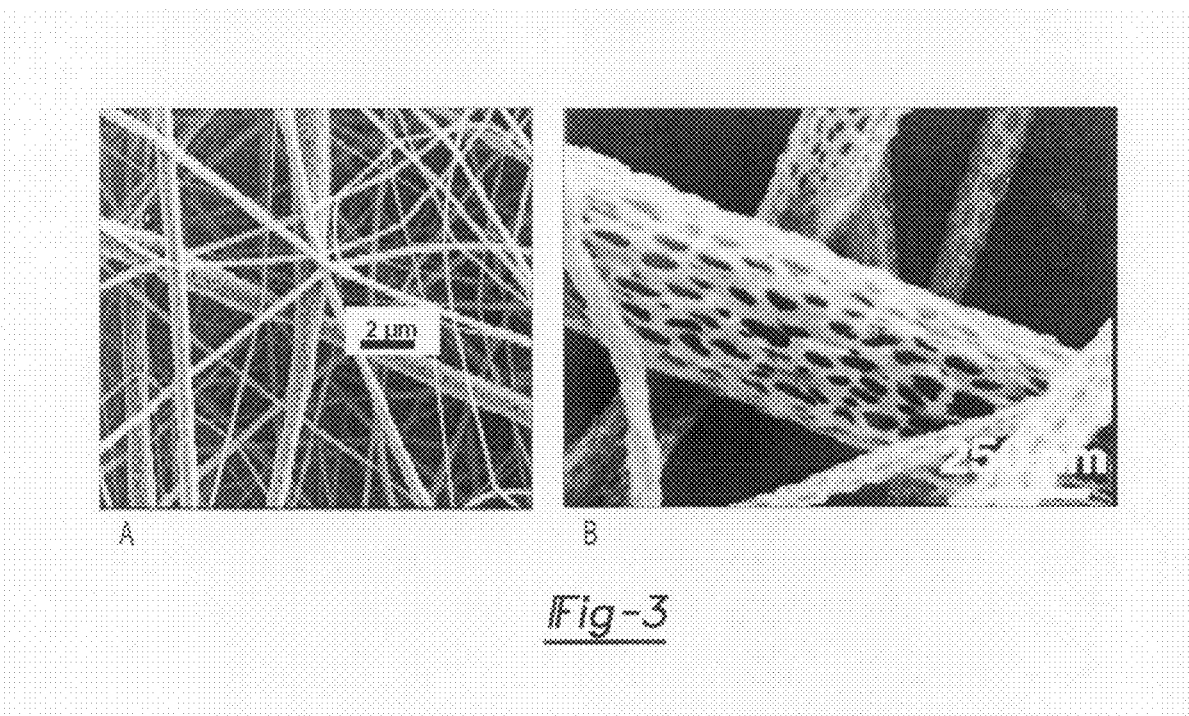
FIG. 3A depicts a scanning electron micrographs of PLGA nanofibers and PEDOT nanotubes
FIG. 3B shows the same nanotubes in higher magnification accordance with the present disclosure.

In some embodiments, the electrospinning process can produce fibers with nanometer diameters in the range of about 10 to about 1000 nm, from about 20 to about 400 nm, from about 50 to about 300 nm, and from about 100 to about 200 nm. As shown in FIG. 3, the nanofibers of PLGA can have diameters ranging from 100-1000 nm with a median diameter ranging between 300-700 nm.

In various embodiments, nanoparticles can be any shape and are generally discrete structures which can include substantially spherical, square, elliptical, polyhedral, polygon, granular and cylindrical shapes. Typically, the nanofibers and nanoparticles can be less than 1 mm in size, less than 0.5 mm, less than 0.1 mm, less than 1000 microns, less than 100 microns or less than 10 microns in size.

Electrically Conducting Polymer Coatings

Figure 1:
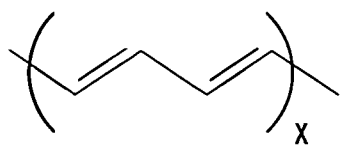
FIG. 1 depicts chemical structures of conducting polymers of a bioactive substance delivery device in accordance with the present disclosure.
Figure 1:
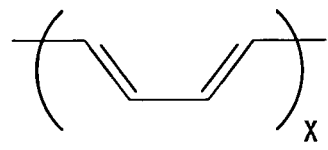
Figure 1:
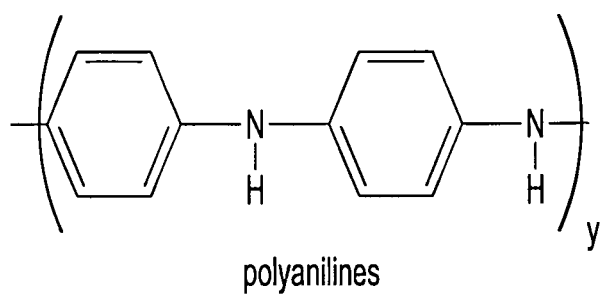
Figure 1:
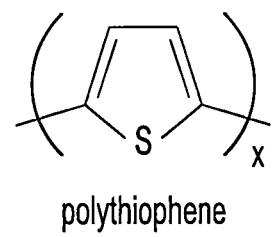
Figure 1:
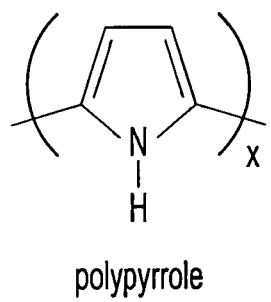
Figure 1:
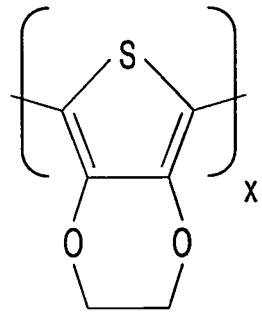

In certain embodiments of the present disclosure, conducting polymers can impart desirable features, for example: are electrically stable over time following implantation in tissue, relatively non-biodegradable yet highly biocompatible, eliciting lower levels of immunoreactivity than commonly used conducting materials such as silicon, platinum, iridium, indium tin oxide, and tungsten. In addition, conducting polymers according to the present disclosure can exhibit properties relating to high electrical conductivity, chemical stability and can be polymerized or deposited in the presence of biocompatible polyelectrolytes, for example, poly(styrene sulfonate) in physiological buffers. As used herein, conducting polymers are polymers capable of conducting electrons and is used interchangeably with conductive polymers. In certain embodiments of this disclosure, the conducting polymers can include, but are not limited to: poly(3,4-ethylenedioxythiophene) (PEDOT), poly(pyrrole), polyanilines, polyacetylenes, polythiophenes, polymer blends thereof, and composites with the ability to conduct electrons or ions, and hybrid polymer-metal materials that are electrically or ionically conducting. Representative structures of some of the conducting polymers are shown in FIG. 1.

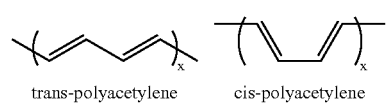

trans-polyacetylene      cis-polyacetylene

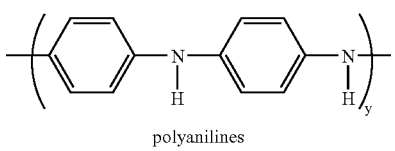

polyanilines

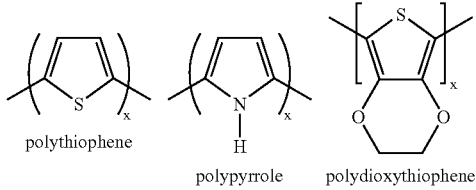
polythiophene    polypyrrole    polydioxythiophene

Illustratively, conducting polymers contemplated by the present disclosure have a conjugated pi-bonded backbone with the ability to delocalize electrons.

Conducting polymers typically require counter ions for polymerization and electroconductivity across the electrode-tissue interface. The conducting polymers are reached with a polyelectrolyte at the molecular level. Electron delocalization is a consequence of the presence of conjugated double bonds in the conducting polymer backbone. To make the conducting polymers electrically conducting, it is necessary to introduce mobile carriers into the double bonds, this is achieved by oxidation or reduction reactions (called "doping"). The concept of doping distinguishes conducting polymers from all other kinds of polymers. This process can be assigned as p-doping or n-doping in relation to the positive or negative sign of the injected charge in the polymer chain by analogy to doping in inorganic semiconductors. These charges remain delocalized being neutralized by the incorporation of counter-ions (anions or cations) denominated dopants. In certain embodiments, ionic electrolytes or dopants used to polymerize conducting polymers include but are not limited to: poly(styrene sulfonate), LiClO4, Phosphate-buffered saline (PBS), Hank's Balanced Salt Solution (HBSS), Collagen, Poly-D-Lysine (PDL), Poly-L-Lysine, poly-ornithine, poly acrylic acid, dodecylbenzene sulfonic acid (DBSA), p-toluenesulfonic acid (p-TSA) and combinations thereof.

The internal texture is replicated from the external texture of PLLA/PLGA electrospun nanofibers. The wall thickness of the PEDOT nanotubes can vary from about 1 nm to about 1000 nm, and the nanotube diameter ranged from about 10 nm to about 2000 nm. By controlling the polymerization time, we could reproducibly prepare tubular structures with thin walls (shorter deposition time) or thick walls (longer deposition time). In various embodiments, the conductive polymer coated nanotubes or nanocavities are electrocontractile, i.e. the conductive nanotubes and nanocavities can contract or dilate upon electrical stimulation and redox of the conducting polymer and surrounding. In some embodiments, the nanotubes and nanocavities whose walls are made of conductive polymers and when provided with the requisite dopants or counterions are able to provide the mass transport required to shunt the bioactive substance out of the nanotube or nanoparticle lumen through pores or other openings in the nanotubes or nanoparticles when the conducting polymer nanotubes or nanocavities are stimulated electrically to contract. In some embodiments, the bioactive substance can be released from the nanotubes or nanoparticles after applying a voltage to the electrically conductive substrate. Upon electrical actuation with a positive or negative voltage ranging from about ±0.1 V to about ±5 V with a scan rate of between 0.01 to 1 V/sec for a period of 0.1 seconds to 6 hours, a total or a specific amount of bioactive substances can be released from the nanotubes.

The degree of contraction or dilation can, depend on several factors that are reproducible and controlled, and can include, the chemical structure of the conducting polymer, the magnitude of charge applied across the electrodes, the nature of the charge, the size of the counterions or dopants used to facilitate electron transduction, and the chemical nature of the counterions, to provide controlled release of the drug from the nanotubes or nanoparticles, in terms of quantity of drug released and rate of drug release. The controlled release of bioactive agents has been unexpectedly and surprisingly reproducible by controlling the magnitude of the voltage applied to the electrode substrate, which in turn actuates the nanotubes and nanoparticles to contract.

To electrochemically control the nanotube actuation, an Autolab PGSTAT 12 (EcoChemie, Utrecht, Netherlands) galvanostat/potentiostat with a conventional four electrode configuration or similarly outfitted power source can be used. In some embodiments, a platinum wire as a counter electrode and Ag/AgCl electrode as a reference electrode can be used. The drug-loaded PEDOT nanotubes can be actuated by applying a positive voltage of 1 V with scan rate of 0.1 V/s for 10 s (charge density 0.8 C/cm$^2$) at one or more specific times. During the reduction of the PEDOT nanotubes (positive voltage bias), electrons are injected into the chains and positive charges in the polymer chains are compensated. In order to maintain overall charge neutrality, negatively-charged counterions are expelled towards the solution and the nanotubes contract. Therefore, PEDOT contraction can produce a mechanical force to create pressure within the nanotubes. The hydrodynamic force inside the nanotubes causes expulsion of nanofiber degradation products and the bioactive substance presumably either through the ends of PEDOT nanotubes or though openings, pores or cracks on the surface of nanotubes created by electrical actuation.

Bioactive Substances

The bioactive substance can include one or more known biologically active substances that do not interfere in the nanofiber or nanoparticle fabrication process. In various embodiments, the bioactive substance can be selected to be admixed with the polymer used for fabricating the nanofiber and can include any drug, pharmaceutical active, growth factor, lipid, steroid, neurotransmitter, enzyme, amino acids, polypeptides, carbohydrates including simple and complex saccharides, polysaccharides and saccharide derivatives, glycoprotein, glycolipid, antineoplastic agent, antiproliferative agent, antithrombogenic agent, anticoagulant, antiplatelet agent, antibiotic, anti-inflammatory agent, gene therapy agent, therapeutic substance, organic drug, pharmaceutical compound, nucleic acids and polynucleotides including DNA, RNA, cDNA, RNAi, antisense agents including siRNA and shRNA, nucleotide mimetics, collagen, collagenic derivative, proteins, or combinations thereof that can be administered or delivered to diagnose, prevent, treat or evaluate any normal or pathological tissue or condition.

In some embodiments, an antisense drug can be delivered in situ by the nanotubes or nanoparticles and may work at the transcription or translation level to interrupt the process by which disease-causing proteins are expressed or produced.

An antineoplastic agent may prevent, kill, or block the growth and spread of cancer cells in the vicinity of an electrode-based nanotube or nanoparticle device, for example a stent. An antiproliferative agent may prevent or stop cells from growing around the electrode based device.

An antithrombogenic agent may actively retard blood clot formation or reduce inflammation at the site of an atherogenic site or plaque occlusion. An anticoagulant may delay or prevent blood coagulation with anticoagulant therapy, using compounds such as heparin and coumarins. Antiplatelet medicinal agents, for example, Plavix® can alter the function of blood platelets, inhibiting their activity in blood coagulation. Antibiotics can kill and/or inhibit the growth of microorganisms and may be used to combat disease and infection. Anti-inflammatory agent may be used to counteract or reduce inflammation in the vicinity of the electrode nanotube or nanoparticle device.

Genetic transformation of surrounding tissue can be accomplished with genetic manipulation techniques commonly known in the art Guidance in the application of such techniques can be found in Ausubel et al. eds., 1995, Current Protocols In Molecular Biology, and in Sambrook et al., 1989, Molecular Cloning: A Laboratory Manual, Cold Spring Harbor Laboratory Press, NY, the contents of which are incorporated herein by reference.

A gene therapy vector comprising Adenovirus, or adeno-associated virus can contain specific DNA sequences, which when used to infect a patient using the appropriate vector vehicle is capable of changing (increasing or decreasing) the expression of a person's gene[s] to treat, cure or ultimately prevent disease. The virus or viral vector contained within the nanotubes or nanoparticles can be released in a strategic and controlled manner to the site enabling the virus to exert the effects of the transgene or RNAi molecule, for example, expression of siRNA or shRNA sequences. The bioactive substance may be any therapeutic substance that reduces, inhibits or ameliorates a disease or disorder. An organic drug can be any small-molecule therapeutic material. A pharmaceutical compound can be any compound that provides a therapeutic effect. A recombinant DNA product or a recombinant RNA product can include any altered DNA or RNA genetic material used to treat a disease. Bioactive substances of diagnostic and/or pharmaceutical value can also include collagen and other proteins, enzymes, for example the enzyme glucose oxidase can be employed as a glucose sensor for use in diabetic patients, saccharides, and their derivatives.

In some embodiments, the electrode based nanotube or nanoparticle devices of the present disclosure can include, without limitation, implantable glucose sensors, deep brain stimulators, cardiac pace makers, "smart" catheters, actuating vascular stents, cortical, cochlear, and retinal prostheses, and automated drug release vehicles. In various embodiments, the bioactive substance can be any medicinal, diagnostic or growth agent used to treat, diagnose or grow tissue of the brain, heart, and musculature. In some embodiments, the electrode based nanotube or nanoparticle devices of the present disclosure can also be used to sense and/or measure ionic or electrical output of electrically active tissues or cells, for example, measure the electrical conductivity of heart cells, brain cells or muscle cells, for example, after a specific medicament or bioactive agent has been released in the vicinity of the recording site. The nanotubes or nanoparticles can sense and measure physiological responses after delivery of a therapeutic or diagnostic agent to determine the biological response of the treated cells or tissues.

Electrode based devices of the present teachings can include devices for use in various heart conditions including coronary restenosis, cardiovascular restenosis, angiographic restenosis, arteriosclerosis, hyperplasia, and other diseases and conditions. For example, the bioactive substance can be selected to inhibit or prevent vascular restenosis, a condition corresponding to a narrowing or constriction of the diameter of the bodily lumen where the stent is placed. The bioactive agent may generally control cellular proliferation, cellular clumping, and chemotaxis. In some embodiments, the control of cell proliferation may include enhancing or inhibiting the growth of targeted cells or cell types, for example proliferating cancerous cells.

B. Methods of Manufacture

Figure 2:
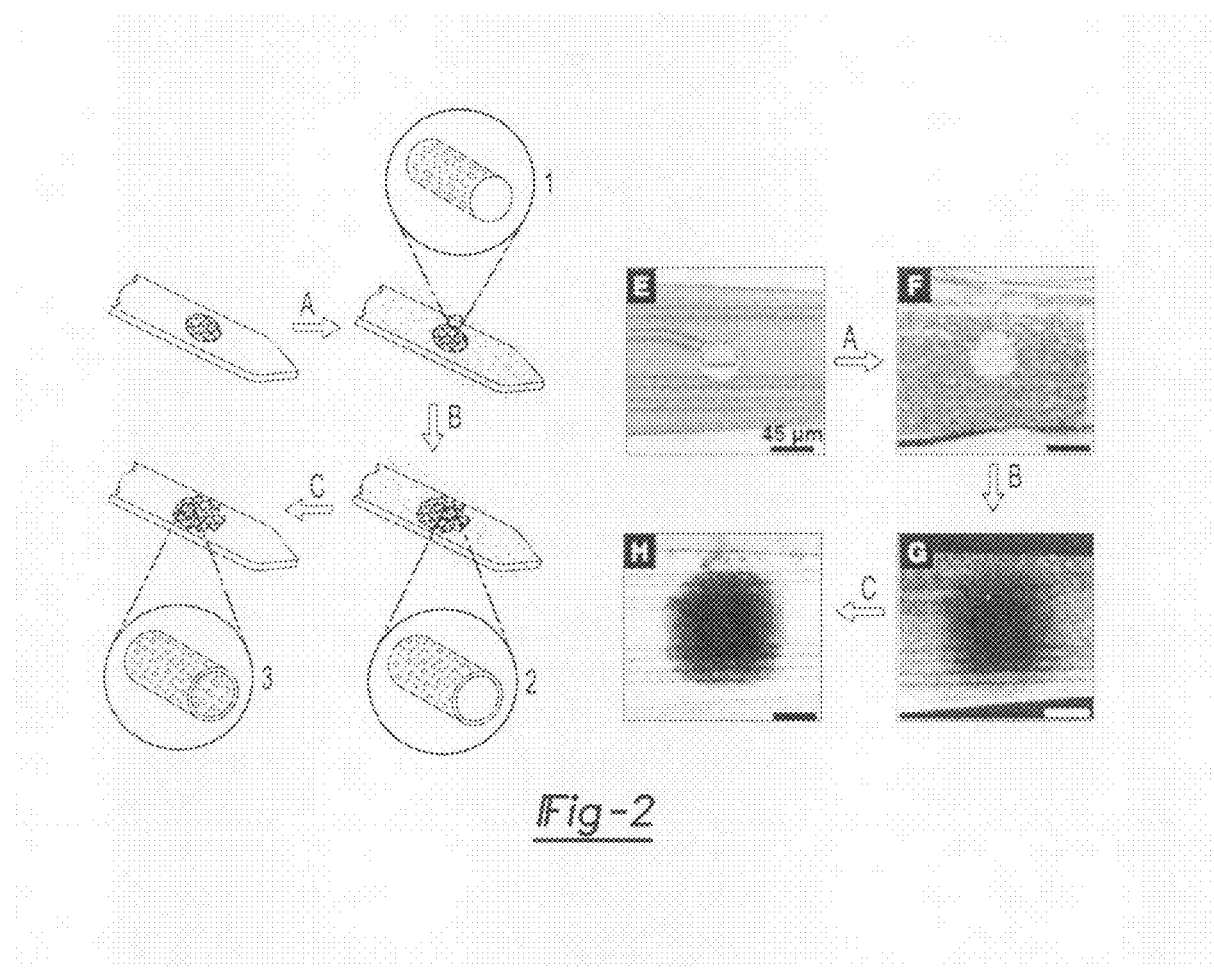
FIG. 2A-FIG. 2C are diagrams illustrating the steps in manufacturing bioactive substance delivery devices in accordance with the present disclosure.
FIG. 2E-FIG. 2F are optical micrographs of the showing stages in the formation of a metal probe coated with nanotubes on the surface in accordance with embodiments of the present disclosure.
Figure 4:
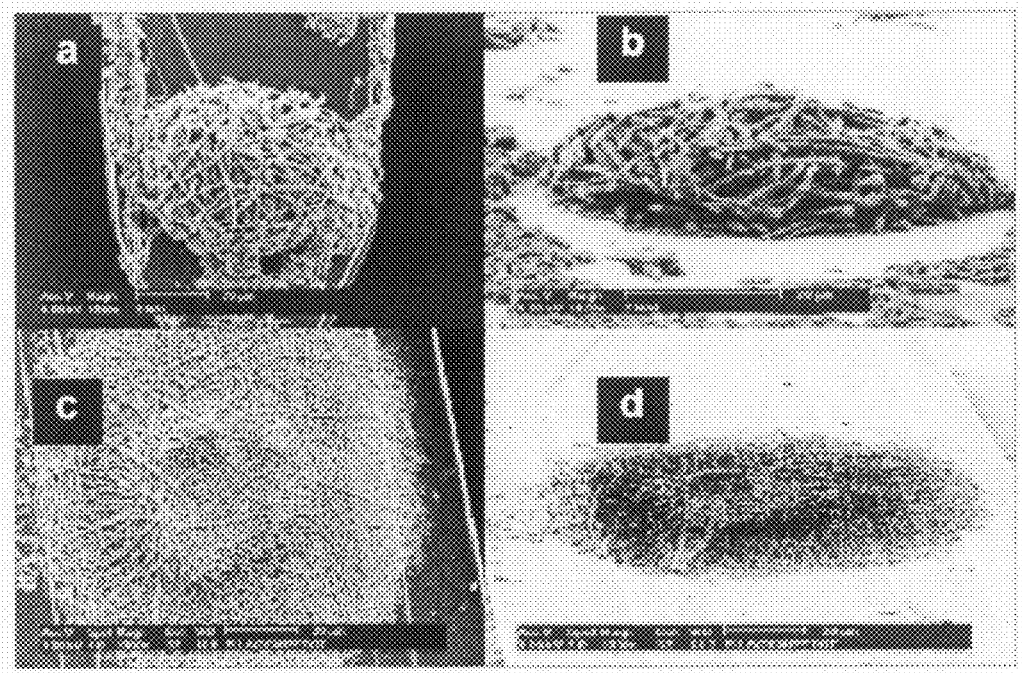
FIG. 4A and FIG. 4B shows scanning electron micrographs of polypyrrole nanotubes and FIG. 4C and FIG. 4D show scanning electron micrographs of polyethylene dioxythiophene (PEDOT) nanotubes on the surface of electrode substrates in accordance with embodiments of the present disclosure.

In various embodiments the electrode based devices are capable of bi-directional electrical conduction and can perform nanoscale to microscale delivery of bioactive substances by applying an electrical current to the conducting polymer nanotubes which in turn release stored drugs, pharmaceuticals, growth factors and other bioactive substances in a controlled and specific manner. The fabrication process can include the steps of providing an electrode substrate on which to apply the nanofibers or nanoparticles. In various embodiments, the electrode substrate can be any device capable of conducting electrons, as shown in FIG. 2 for example, microfabricated neural prosthetic devices and probes FIG. 2E. The nanofibers or nanoparticles can be synthesized and applied onto the electrode substrate through the process of electrospinning, meltspinning and fiber extrusion as shown in FIGS. 2B and 2F. In various embodiments, the nanoparticles can include structures of various shapes, lengths and orientations. In some embodiments, the bioactive substance(s) can be encapsulated in geometries other than fibers, for example, nanospheres, nanocylinders and nanodroplets, etc. The polymers used to manufacture the nanofibers can be loaded and mixed with the bioactive substance or substances of choice. The nanofibers are then applied around the electrode substrate as shown in FIG. 2F. In some embodiments, a plurality of nanofibers (meaning 2 or more) can be applied to a surface of an electrode substrate. The nanofibers or nanoparticles can be placed on the surface of the electrode substrate, as shown in FIG. 4 (a-d), alternatively, a coating of conducting polymer can be placed on the electrode substrate surface, followed by the placement of nanofiber or nanoparticles on the conducting polymer. The electrode substrate in at least partial contact or indirect contact with degradable nanofibers or nanoparticles can then be coated with electrically conducting monomers, for example pyrrole and/or EDOT and the appropriate dopant, for example, any type of anion/cation such as polystyrene sulfonate (PSS) (large molecules), Lithium Perchlorate (small molecules), and then electrochemically polymerized around the nanofibers, by applying a current in galvanostatic or a voltage in potentiostatic mode with conventional four electrode configurations as shown in FIGS. 2G and 2H. Methods used in the electrochemical polymerization is described in "Ordered surfactant-templated poly(3,4-ethylenedioxythiophene) (PEDOT) conducting polymer on microfabricated neural probes" Yang et al., ActaBiomaterialia (2004) and is incorporated herein in its entirety.

Figure 5:
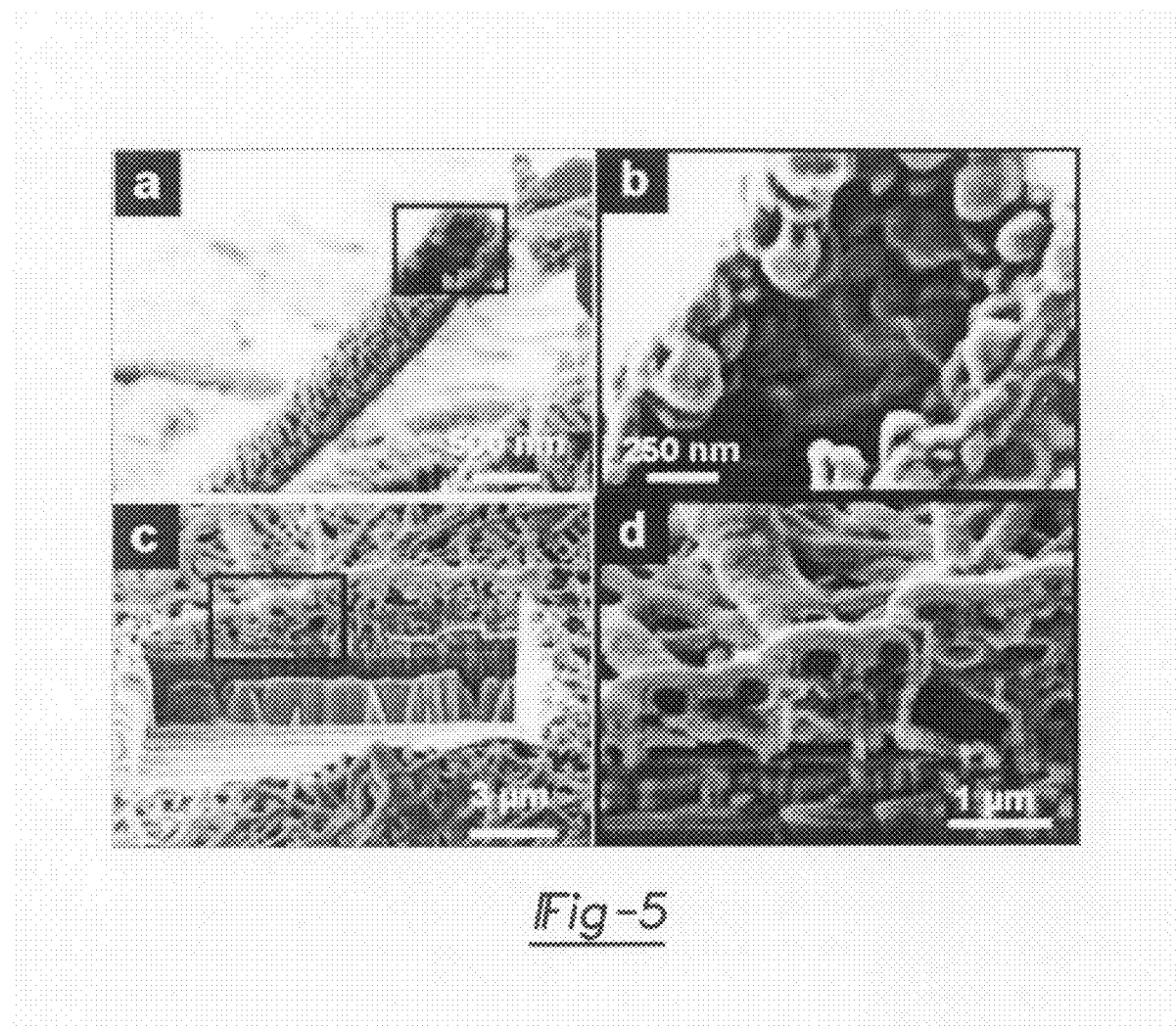
FIG. 5A shows a scanning electron micrograph of a single PEDOT nanotube in accordance with the present disclosure.
FIG. 5B shows a scanning electron micrograph of A at higher magnification in accordance with the present disclosure.
FIG. 5C shows a scanning electron micrograph section of conducting polymer nanotubes cut with Focused Ion Beam showing the various layers and PEDOT nanotube coating in accordance with the present disclosure.
FIG. 5D shows a higher magnification of FIG. 5C in accordance with the present disclosure.

In various embodiments, the conducting monomers can be polymerized upon the nanofibers or nanoparticles containing one or more bioactive substances. As shown in FIG. 3 the conducting polymer coated nanofibers or nanoparticles can include pores of various sizes ranging from about 1 nm to about 200 nm but are generally less than the diameter of the nanofiber or nanoparticle. The pores can be distributed randomly along the length of the coated nanofiber or nanoparticle and in some instances pores or openings are found at the terminal ends of the nanotubes as shown in FIG. 5.

Conducting polymers can also be applied around the nanofibers using oxidative polymerization and chemical vapor deposition (CVD). Oxidative polymerization of conducting polymers of pyrrole and ethylenedioxythiophene contemplated in the present disclosure are commonly used in the field, including methods described by Hatano, T. et al., (2004) Chemistry, 10:5067-75.

In some embodiments, the electrode substrate can be coated on one surface with one nanostructure, for example nanofibers loaded with one type of bioactive substance, while another electrode substrate surface or portion of electrode substrate surface is coated with a second nanoparticle or nanofiber containing a different bioactive substance to form bi-phasic particles wherein one bioactive substance is released with one kind of electrical stimulus, and whereas the second bioactive substance is released with a reverse charge or a voltage bias of the same or different magnitude.

In some embodiments, the nanofibers or nanoparticles can be degraded prior to implantation using an acceptable solvent, for example, dichloromethane when using PGLA nanofibers as shown in FIG. 6, leaving behind the bioactive substance in the conducting polymer nanotube or nanoparticle lumen (See FIG. 6C-6D.) In some embodiments, when the nanofiber or nanoparticle containing the one or more bioactive substances is degraded either with an acceptable solvent which does not chemically alter, degrade, denature or reduce substantially the activity of the bioactive substance or naturally, over time after coating with conducting polymer, the residual space occupied previously by the nanofiber or nanoparticle is defined as the lumen and is surrounded by a coating of conducting polymer. In some embodiments, the nanofibers or nanoparticles can be slowly degraded in-situ leaving behind the bioactive substance(s) trapped in the conducting polymer nanotubes. See FIG. 6.

In some embodiments, cells can be grown on the surface of the electrode substrate prior to application of bioactive substance loaded nanofibers or nanoparticles, or cells may be grown in the crevices and pores of the nanofiber network prior to the application of the conducting monomer and electrochemical polymerization step. In some embodiments, the electrode substrate having a network of nanofibers or nanoparticles on the surface or surfaces of the electrode substrate can be implanted into tissue or hydrogel scaffolds. EDOT and/or pyrrole can be delivered to the electrode substrate-nanofiber network and polymerized in-situ (in tissue) or in a hydrogel scaffold containing cells providing for cell and nanofiber templated nanotubes containing one or more bioactive substances.

C. Methods of Use

In certain embodiments, the present devices can be useful for example, in the manufacture of improved microelectromechanical systems (MEMS), electrode-based devices for long-term implantation in the central nervous system (CNS). The present disclosure can also be applied to the development of new generation of cardiac and musculoskeletal electrophysiological devices and implantable electrical and biomolecule sensors and drug delivery devices. In various embodiments, the present disclosure provides for devices that can be electrically stable, bioactive, and rendered highly biocompatible having biomaterials that are readily adaptable to existing and future biomedical device technologies. Devices for sensing, recording and drug delivery in accordance with the present disclosure can be incorporated into the development of the next generation of MEMS devices, providing improvements in reliability, performance, and reductions in size and cost. In some embodiments, the microelectrode-based biomedical devices contemplated by the present disclosure can be used for long-term implantation in the body to treat patients with paralysis, sensory deficits and chronic pain and diseases such as Parkinson's disease, Alzheimer's disease, epilepsy, heart disease, diabetes, and cancer.

In some embodiments method for treating a disease in a patient, comprises the steps of providing an electrically mediated drug delivery device. The device comprises (A) a first and second electrically conductive substrate; (B) a plurality of electrically contractile nanotubes in contact with at least a portion of the first electrically conductive substrate. The plurality of the nanotubes have at least one opening, pore or aperture. Some of the nanotubes have a lumen containing at least one bioactive substance that is effective in treating the disease. The bioactive substance can be released by electrically actuating the nanotubes with a power source operably connected to either one of a first and a second electrically conductive substrate or electrode. The device can be placed in contact with or near a treatment site in the patient. The bioactive substance can be released when a voltage is applied to at least one of the first and second electrically conductive substrates or electrodes of the device. In this way, a current is supplied to the electrically conductive nanotubes, thereby causing contraction of the nanotubes and concomitant release of the one or more bioactive substance from the lumen of the nantotube through an opening at or near the treatment site.

In some embodiments of the present disclosure, the devices disclosed herein can be used to provide for electrical stimulating and sensing that can facilitate drug and bioactive substance delivery in a controlled and specific manner. There are numerous configurations of the electrode substrate coated with nanotubes and/or nanoparticles having drug delivery and nanofiltration capabilities presently contemplated by the present disclosure which can be successfully practiced. In various embodiments, the present disclosure can be adapted to create fully integrated and more efficacious implanted electrodes for cortical recording/stimulation, deep brain stimulators, peripheral nerve electrodes, cardiac anti-arrythmia devices, muscle stimulation, surgical ablation (epilepsy treatments), pH monitoring, glucose sensing, cochlear implants, and retinal prosthetics.

The devices described herein can be connected to power supplies which can include a battery, a direct wire to a DC or AC power source, and can further include one or more switches or variable resistors to control the electrical signal inputted to the conducting monomers for electrochemical polymerization and/or for stimulating the nanotubes or nanoparticles to release stored bioactive substances to adjacent or localized target cells or tissues. In various embodiments, the power source can be connected to a counter electrode and/or reference electrode. In some embodiments, while in use, the electrodes can be in contact with a physiological medium such as spinal fluid, blood, neurons, brain, heart and muscle tissue. The devices can also be connected to sophisticated current delivery devices and computers/CPUs, including pulse generators, radio frequency modulators, counters and recorders for electrical output and recording functions. Furthermore, in addition to the advanced biomimetic features of the electrode substrate coated at least with a portion of nanotubes and nanoparticles, the ability to deliver bioactive substances in response to electrical stimulation provides a novel and improved modality in disease treatment and tissue regeneration. Moreover, drug loaded conducting polymer nanotubes and nanoparticles are highly biocompatible, having low electrical impedance, cell-attracting, high surface area, electrically active coating for electrode-based biomedical devices.

The present disclosure provides conducting nanotube or nanotubullar structures for precisely controlled release of one or more drug for electrically sensing and stimulating biomedical device applications. Targeted delivery by the electrically conducting nanotubes and nanoparticles can be performed precisely by releasing individual drugs and bioactive substances at desired points in time using electrical stimulation of conducting polymers. In accordance with the present disclosure, the methods described herein provide a generally useful means for creating low impedance, biologically active polymer coatings which can facilitate integration of electronically active devices with living tissues. Other biomedical applications of the devices encompassed by the present disclosure include: molecule-eluting, electrically active polymer nanotubes facilitating highly localized stimulation of neurite outgrowth and guidance for neural tissue regeneration using neuronal growth and differentiation factors.

In some embodiments, the present disclosure provides for sensing devices having spatially and temporally controlled drug delivery for ablation and pharmacological alteration of specific cell populations. The drug and bioactive substance loaded nanotubes and nanoparticles of the present disclosure can also be used for functionalizing microelectrodes on neural prostheses and biosensors. However, the electrically conducting drug delivery devices comprising an electrode substrate, having a network of electrically conductive nanotubes comprising biocompatible non-degradable polymers or nanoparticles loaded with bioactive substances previously coated with conducting, biocompatible, non-degradable polymers can also be expected to be applied in a broad range of fields such as organic chemistry, biomedical engineering, and pharmacology. The improved design represents a new generation of biomaterials that can interact with living tissue including cells within and adjacent to biomedical device implantation sites via signaling mechanisms that have until recently, been the exclusive domain of cells themselves.

In some embodiments, a suitable microfluidic device can be devised to function as a miniaturized sensitive biosensor. The microfluidic device comprises a substrate having a plurality of conduits or microchannels for ingress and egress of various fluids, analytes and reagents. The substrate can be made of any biocompatible material, for example, silicon, silicon derivatives, plastic, polyolefin, glass or ceramic. In at least one of the microchannels is in fluid communication with one or more microelectrodes that can be machined or coupled to the surface of the substrate to measure the conductivity of the solution in a reaction channel or chamber. The reaction chamber may also optionally contain conductive polymer nanotubes or nanoparticles that can sense and transmit changes in redox state, ionic activity and/or measure transfer of electrical charge between chemical species, for example an enzyme and its mediator and/or substrate. Suitable dimensions for the microchannels can be in the range from about 1 micron to about 1 nanometer, or from about 10 microns to about 1000 microns, or from about 20 microns to about 500 microns or from about 50 microns to about 100 microns.

In some embodiments, a biological sensor comprising a substrate made of glass, ceramic, silicon, plastics including: polycarbonate, polystyrene or polydimethylsiloxane (PDMS). The sensor can contain one or more inlet microchannels for receiving a sample for example, microchannel no. 1 (fluid no. 1), a reaction chamber (reaction no. 1). A separate fluid inlet microchannel (fluid no. 2) is also open to reaction chamber no. 1, but is not in fluid communication with microchannel no. 1. The reaction chamber has a plurality of PEDOT conductive nanotubes in electrical communication with at least one metal electrode, for example a platinum electrode. Other reference and/or working electrodes can be machined into the reaction chamber to provide an electrical field to detect redox reactions occurring between an analyte and target enzyme, for example, by cyclic voltammetry.

Practical application of such a biological sensor can include glucose detection with lithographical deposited PEDOT nanotubes loaded with glucose oxidase in a physiological buffer. Prior to qualitative or quantitative detection of plasma or serous glucose, standard curves using known concentrations of glucose are first used to extrapolate the detection limits of the microfluidic device. Glucose detection can be performed by contacting a mediator solution such as ferrocene carboxylic acid with a 15 mM glucose solution in a test tube outside the microfluidic device. This solution is then injected in the microchannel and a cyclic voltammetry experiment is performed. The detection of glucose in such a microfluidic device can be shown by presence of the catalytic shape of the voltammogram, meaning that the mediator is reduced and oxidized by the enzyme and the electrode respectively. Detection of glucose is possible within this microfluidic device. This procedure is repeated with different concentrations of glucose, except, the glucose oxidase is contained within the conductive polymer nanotubes. Electrical actuation of the conductive polymer nanotubes using the electrode in the reaction chamber, releases an amount of glucose oxidase to react with the glucose and the mediator.

In some embodiments, samples of patient serum or plasma can be injected (10-1000 nL) into microchannel no. 2 and the mediator is injected into microchannel no. 1. A predetermined voltage is applied to the nanotubes to release a predetermined amount of glucose oxidase from the lumen of the nanotube. The amount of test analyte, glucose present in the serum or plasma can be detected by sweeping the field in the reaction chamber using the reference electrode and working electrode with a specific voltage range and extrapolating the amount of glucose from a standard curve. Multiple samples can be multiplexed and injected into the microfluidic device and quantitatively analyzed.

In other embodiments, different enzyme/substrate or antibody/antigen detection systems can be similarly designed and implemented using microfluidic biosensors described herein implementing the electrically actuated nanotubes and nanoparticles to deliver specific amounts of enzyme/antigen or antibody/antigen for quantitative and qualitative analysis. One of ordinary skill in the art can substitute the bioactive substance embedded within the lumen of the nanotubes to identify several other important analytes that are diagnostically or clinically important. For example, cancer antigens, for example, prostate serum antigen, CA, 19-9, CEA, EGFr, p53, p27, can be screened and measured using the microfluidic devices disclosed herein. Other markers, for example, Alzheimer's disease specific agents such as amyloid-beta peptide can be detected when the bioactive substance is an antibody to said marker. Similarly, markers for cardiac diseases and conditions such as myocardial infarction can be determined using test analytes related to cardiac arrest such as: troponin I, troponin T, myoglobin, using cardiac marker specific antibodies as the bioactive substance.

In certain embodiments of the present disclosure, cells entrapped in the conducting nanotube scaffold can include stem cells or neural progenitor cells. Electrical stimulation to the neural progenitor cells and delivery of neural growth factors represents a novel biosynthetic paradigm that can be performed ex-vivo and/or in-situ at the point of tissue disease or trauma. In addition to recording and pulsing electrical signals in surrounding tissue, tissue regeneration near the implanted cell-based conducting nanotube or nanoparticle device can be facilitated due to processes stimulated by the implanted stem/progenitor cells such as growth factor secretion, recruitment of endogenous stem cells to tissue injury sites, and triggering of endogenous neurogenesis. In some embodiments, the drug and bioactive substance releasing nantotubes and nanoparticles can provide for cell patterning thus allowing cells to migrate along the nanotubes and other nanoparticles. These processes can also help circumvent the harmful early stages of the immune response that is normally generated by insertion of a foreign body into a tissue.

In certain embodiments of the present disclosure, the conducting polymer nantotubes or nanoparticles can be directly deposited within living tissue thereby reducing the likelihood of electrode damage and tissue damage during and after electrode implantation. In certain embodiments, the resulting cell-based conducting electrode can be in intimate contact with the plasma membrane of living cells. In certain embodiments, the growth of the 3-dimensional nanotube network from the surface of the implanted bioactive substance drug delivery device comprising electrospun nanofibers loaded with bioactive substances can create an electrically-connected diffuse network of molecularly thin polymer nanotubes or other nanoparticles, such as nanospheres woven around cells, effectively innervating the tissue.

In certain embodiments of present disclosure, the electrode substrate comprising bioactive substance loaded nanofibers can be coated with conducting monomers such as pyrrole and ethylenedioxythiophene and subsequently polymerized within living tissue resulting in fully integrated and efficacious implanted electrodes, for example, but not limited to: cortical recording/stimulation, deep brain stimulators, peripheral nerve electrodes, cardiac anti-arrythmia treatments (for example AV nodal reentry tachycardia and other arythmias), muscle stimulation, surgical ablation (for example epilepsy treatments), pH monitoring, glucose sensing, cochlear implants, and retinal prosthetics.

In certain embodiments according to the present disclosure, the biocompatible implantable nanoscale bioactive substance delivery devices can also be implemented into hydrogel seeded with living cells. In some embodiments, the electrode substrate having a diffuse network of electrospun nanofibers loaded with one or more bioactive substances can be directly implanted into hydrogel scaffolds comprising inert natural and synthetic matrix components such as alginates, collagen, gelatin actin and other extracellular matrix components. In some embodiments, the hydrogel can be seeded with cells, including stem and other progenitor cells, myocytes, neurons, and electrically active cells. In preparing the bioactive substance delivery device comprising the bioactive agent loaded nanofibers, electrode substrate and cell seeded hydrogel scaffold. In some embodiments, the electrode and nanofibers can be coated in part or in total with conducting monomer. In some embodiments, the nanofibers and hydrogel scaffold can be coated with conducting polymers after polymerization of the conducting monomers around the nanofibers and at least a portion of the electrode substrate. The biocompatible hydrogel polymer serves as both a nutritive and physically supportive environment for the living cells and as a scaffold for creation of a diffuse conducting polymer electrode network of micrometer and nanometer thin nanotubes capable of nanoscale and precise bioactive substance delivery. In certain embodiments, the hydrogel materials can be exceptionally soft, hydrophilic and "tissue-like" thus well-suited for coating of biomedical devices making possible low levels of traumatic injury to host tissue during device implantation.

EXAMPLES

Example 1

Conducting Polymer Electrodes with Drug Filled Nanotubes

PLLA and PLGA were considered as suitable polymers for the template since they can be readily processed into nanoscale fibers. Nanofibers of biodegradable PLLA or PLGA were first electrospun onto the surface of neural probe followed by electrochemical deposition of conducting polymers around the electrospun nanofibers. PLLA/PLGA nanofibers and PLGA nanofibers loaded with dexamethasone were prepared by electrospinning. PLLA solution was prepared by dissolving 0.72 g PLLA in 10 ml of chloroform at a temperature of 50° C. for 10 hr in order to have a homogenous solution with PLLA concentration of 4% (w/v). The PLGA solutions consisting of 2.7 g PLGA and 10 ml chloroform were stirred at a temperature of 55° C. for 5 hr in order to make a homogenous solution with a concentration of 15% (w/v). Also a mixture of 2.5 g PLGA and 0.675 g dexamethasone was added. The nantotubes were subsequently coated with conducting monomers EDOT and pyrrole and electrochemically polymerized on electrode sites and PGLA loaded dexamethasone nanofibers. After polymerization, the PGLA core fibers were removed by soaking the coated probe in dichloromethane. The electrochemical process was performed for acute and chronic probes on each electrode site by an Autolab PGSTAT 12 (EcoChemie, Utrecht, Netherlands) in galvanostatic mode with a conventional four electrode configuration at room temperature. EDOT monomer (21.4 µl) and Py monomer.

To electrochemically control the nanotube actuation, Autolab, PGSTAT 12 (EcoChemie, Utrecht, Netherlands) galvanostat/potentiostat, was used with a conventional four electrode configuration. A platinum wire was used as a counter electrode and Ag/AgCl electrode as a reference electrode. The drug-loaded PEDOT nanotubes were actuated by applying a positive voltage of 1 V with scan rate of 0.1 V/s for 10 s at the five specific times for 15 samples. FIG. 6 panel G shows the release of dexamethasone from conducting polymer nanotubes, indicating that at five different time intervals the release of dexamethasone from conducting polymer nanotubes could be greatly increased after electrical stimulation FIG. 6, panel G.

An Autolab PGSTAT 12 and Frequency Response Analyzer (FRA) software were used to record impedance spectra of electrode sites for 10 neural probes. Cyclic voltammetry (CV) was used to investigate the charge transfer capacity through the electrodes after surface modification with the PEDOT nanotubes (See FIG. 7B). The microelectrode was swept through a potential of −0.9 to 0.5 V at a scan rate of 100 mV/s. As shown in FIG. 7A, probes having coatings of electrically conducting nanotubes result in electrodes having lower impedance and higher charge transfer capacity as compared to bare metal (gold) electrodes. Electrochemical impedance spectroscopy (EIS) was used to explore the conductivity of the polymer coatings over a frequency range from 1 Hz-100 kHz. The impedances at 1 kHz are particularly important because they correspond to the characteristic frequency of neuronal action potentials. The electrode's impedance across all frequencies was moderately increased by electrospinning of the nonconductive layer of PLGA fibers. Specifically the impedance at 1 kHz was increased by about 2 orders of magnitude (FIG. 7A). However, this impedance was significantly decreased by the subsequent deposition of the conducting polymer nanotubes and specifically the impedance at 1 kHz was decreased by about 4 orders of magnitude, a net decrease of 2 orders of magnitude from unmodified electrode (FIG. 7A). By monitoring the impedance as a function of deposition time at 1 kHz, it was found that the impedance initially decreased dramatically and then slowly increased, as has been seen previously for other conducting polymer films.

The initial impedance of the bare gold sites was 800±20 kΩ for acute (1250 µm$^2$) and 4±0.08 MΩ for chronic (1600 µm$^2$) probes at 1 kHz. The corresponding values of impedance were decreased to a minimum of 8±2 kΩ (acute probes, after 18 μC of total deposition charge) and 1 kΩ (chronic probes, after 18 μC of total deposition charge) by growing PEDOT around the PLGA nanofibers. These values were further reduced to 4±1 kΩ (acute) and 800±85 Ω (chronic) after removing the PLGA template fibers and creating nanotubular PEDOT (FIG. 7A). These extremely low values of electrode impedance are expected to significantly enhance the performance of these probes in-vivo. This method has resulted in the largest decrease of the 1 kHz impedance multiplied by electrode area (5 MΩ*μm$^2$ for acute and 1.3 MΩ*μm$^2$ for chronic) of any coating design presently known.

SEM images of electrode sites showed the growth of PEDOT around the PLGA fibers after electrochemical deposition. PEDOT nucleated on the gold at the electrode site and has grown around the PLLA/PLGA nanofibers to create a 3D mesh of PEDOT nanofibers. After the electrical excitation of the conducting nanotubes containing dexamethasone, we observed a significant increase in the amount of dexamethasone released.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A biocompatible electrode comprising:
a first electrically conductive substrate; and
a second electrically conductive substrate which comprises a plurality of electrocontractile nanotubes comprising walls of conductive polymer defining lumens or cavities therein containing at least one bioactive substance, said second electrically conductive substrate contacting at least a portion of said first conductive substrate;
wherein electrical actuation of said nanotubes induces contraction of said nanotube walls causing the release of at least a portion of said bioactive substance from said lumens or cavities.

2. A sensor device comprising:
(1) a substrate having one or more sealed microchannels and at least one reaction chamber forming a microfluidic assembly;
(2) a power source capable of providing a voltage to said microfluidic assembly; and
(3) a data recorder for recording changes in electronic signals provided by said microfluidic assembly;
the microfluidic assembly comprises:
(i) a reaction chamber comprising the electrode of claim 1
wherein release of said bioactive substance enables binding of said bioactive substance with a test analyte thereby producing a change in electronic signal capable of being transduced by said microfluidic assembly to said data recorder.

3. The sensor device according to claim 2, wherein the target analyte is selected from the group consisting of glucose, troponin I, troponin T, myoglobin, prostate serum antigen, CA, 19-9, CEA, EGFr, p53, p27, and amyloid-beta peptide.

4. A method for controlled release of a bioactive substance in a biological tissue, comprising the steps:
(i) providing a biocompatible electrode according to claim 1 and a power source operably connected to said first and second conductive substrates;
(ii) placing said electrode in contact with the biological tissue, and
(iii) applying a voltage to at least one of said first and said second electrically conductive substrates of said electrode so as to supply a voltage to said nanotubes, thereby causing a contraction of said nanotube walls and concomitant release of said bioactive substance.

5. The method according to claim 4, wherein the bioactive substance is released from said nanotubes after applying to said at least one of said first and said second electrically conductive substrate a voltage ranging from about +0.1 V to about +5 V with a scan rate of between 0.01 to 1 V/sec for a period of 0.1 seconds to 6 hours.

6. The method according to claim 4, wherein said conductive polymer comprises poly(3,4-ethylenedioxythiophene) (PEDOT), poly(pyrrole), polyanilines, polyacetylenes, polythiophenes, or polymer blends thereof.

7. The method according to claim 4, wherein said plurality of nanotubes are formed on at least a portion of said first electrically conductive substrate comprising the steps:
(i) electrospinning a solution comprising a biodegradable polymer and at least one bioactive substance onto at least a portion of a surface of said first electrically conductive substrate thereby forming a mesh of nanofibers in contact with said first electrically conductive substrate;
(ii) electrochemically depositing a conductive polymer around said nanofibers forming a plurality of nanotubes; and
(iii) degrading said biodegradable polymer of said nanofibers with a solvent, thereby leaving said at least one bioactive substance inside a lumen or cavity of said nanotubes.

8. The method according to claim 7, wherein the concentration ratio of biodegradable polymer to bioactive substance ranges from 1:99 to 99:1.

9. The method according to claim 7, wherein the conductive polymer comprise poly(3,4-ethylenedioxythiophene) (PEDOT), poly(pyrrole), or polymer blends thereof.

10. The method according to claim 7, wherein the biodegradable polymer comprises a member selected from the group consisting of poly(D-lactic acid) (PDLA), poly(L-lactic acid) (PLLA), poly(lactide-co-glycolide) (PLGA) poly (glycolic acid) (PGA), and their derivatives, poly(epsilon caprolactone) (PCL), chitosan, nylon, PEOxide, alginates, poly vinyl alcohol and combinations thereof.

11. A method for treating a disease site in a patient, comprising the steps:
(i) providing a biocompatible electrode according to claim 1 and a power source operably connected to said first and said second electrically conductive substrates;
(ii) placing said electrode in contact or near the disease site in said patient,
(iii) applying a voltage to at least one of said first and said second electrically conductive substrates of said electrode so as to supply current to said electrically conductive nanotubes, thereby causing contraction of said nanotubes and concomitant release of said bioactive substance at or near the disease site.

12. The method according to claim 11, wherein the disease is selected from the group consisting of neurological disease, cardiac disease, cardiovascular disease, muscular disease, endocrinology disease, immunological disease, circulatory disease and combinations thereof.

13. The method according to claim 11, wherein the disease to be treated is any one or more of Parkinson's disease, muscular dystrophy, Alzheimer's disease, epilepsy, diabetes, and coronary artery disease.

14. The biocompatible electrode according to claim 1, wherein the first and second electrically conductive substrates independently comprise a metal, a carbon composite, silicon, a metal oxide, conductive polymer, or combinations thereof.

15. The biocompatible electrode according to claim 1, wherein the conductive polymer comprises poly(3,4-ethylenedioxythiophene) (PEDOT), poly(pyrrole), polyanilines, polyacetylenes, polythiophenes, or polymer blends thereof.

16. The biocompatible electrode according to claim 1, wherein the conductive polymer comprises poly(3,4-ethylenedioxythiophene) (PEDOT).

17. The biocompatible electrode according to claim 1, wherein the conductive polymer further comprises a dopant selected from the group consisting of poly(styrene sulfonate), $LiClO_4$, phosphate-buffered saline (PBS), Hank's Balanced Salt Solution (HBSS), collagen, poly-D-lysine (PDL), poly-L-lysine, poly-ornithine, poly acrylic acid, serum, dodecylbenzene sulfonic acid (DBSA), p-toluenesulfonic acid (p-TSA), and combinations thereof.

18. The biocompatible electrode according to claim 1, wherein the bioactive substance is selected from the group consisting of a pharmaceutical active, a growth factor, a polypeptide, a lipid, a nucleic acid, a amino acid, a receptor, a steroid, a carbohydrate, a glycoprotein, a glycolipid, a neurotransmitter, an antineoplastic agent, an antiproliferative agent, an antithrombogenic agent, an anticoagulant, an antiplatelet agent, an antibiotic, an anti-inflammatory agent, a gene therapy agent, a therapeutic substance, and combinations thereof.

19. The biocompatible electrode according to claim 1, wherein the nanotubes comprise a diameter ranging from about 10 nm to about 1000 nm.

20. The biocompatible electrode according to claim 1, wherein the nanotubes comprise a wall thickness ranging from about 1 nm to about 500 nm.

21. The biocompatible electrode according to claim 1, further comprising a power source operably connected to the first and second conductive substrates.

22. The biocompatible electrode according to claim 1, wherein a hydrogel scaffold comprises the second electrically conductive substrate, the hydrogel scaffold being coated with a conducting polymer.

* * * * *